US008377908B2

(12) United States Patent
Grases Freixedas et al.

(10) Patent No.: US 8,377,908 B2
(45) Date of Patent: Feb. 19, 2013

(54) FIXED-DOSE ASSOCIATION OF PHYTATE AND ZINC

(76) Inventors: Felix Grases Freixedas, Palma de Mallorca (ES); Joan Perello Bestard, Inca (ES); Bernat Isern Amengual, Consell (ES); Pilar Sanchis Cortes, Palma de Mallorca (ES); Rafael M Prieto Almirall, Palma de Mallorca (ES); Antonia Costa Bauza, Illes Balears (ES)

( * ) Notice: Subject to any disclaimer, the term of this patent is extended or adjusted under 35 U.S.C. 154(b) by 597 days.

(21) Appl. No.: 12/279,616

(22) PCT Filed: Feb. 14, 2007

(86) PCT No.: PCT/EP2007/051413
§ 371 (c)(1),
(2), (4) Date: Aug. 15, 2008

(87) PCT Pub. No.: WO2007/093611
PCT Pub. Date: Aug. 23, 2007

(65) Prior Publication Data
US 2009/0035232 A1    Feb. 5, 2009

(30) Foreign Application Priority Data
Feb. 17, 2006   (ES) .................................. 200600377

(51) Int. Cl.
*A61K 31/6615* (2006.01)
*A61P 19/10* (2006.01)
(52) U.S. Cl. ........................................ 514/102
(58) Field of Classification Search .................... 514/102
See application file for complete search history.

(56) References Cited

U.S. PATENT DOCUMENTS

| 3,488,419 | A |   | 1/1970  | McCune et al. |
|-----------|---|---|---------|---------------|
| 3,934,001 | A |   | 1/1976  | Watson |
| 4,215,105 | A |   | 7/1980  | Gaffar et al. |
| 4,259,316 | A |   | 3/1981  | Nakashima et al. |
| 4,515,772 | A |   | 5/1985  | Parran, Jr. et al. |
| 4,627,977 | A |   | 12/1986 | Gaffar et al. |
| 4,808,401 | A |   | 2/1989  | Gaffar et al. |
| 5,300,289 | A | * | 4/1994  | Garlich et al. .................. 424/54 |

FOREIGN PATENT DOCUMENTS

| CN | 1593376        | 3/2005 |
| GB | 2055574 A      | 3/1981 |
| WO | WO 2005/044278 | 5/2005 |

OTHER PUBLICATIONS

Straub, Current Opinion in Urology, Mar. 2005: 15(2): pp. 119-126, abstract only.*
Lo (Effect of Phytate: Zinc Molar Ratio and isolated Soybean Protein on Zinc bioavailability, The Journal of Nutrition, 111: p. 2223-2234, 1981).*
Grases, F., et al.; Effects of Phytic Acid on Renal Stone Formation in Rats, *Scandinavian Journal of Urology and Nephrology*, Scandinavian University Press, Stockholm, Sweden, vol. 32, No. 4, 1998, pp. 261-265.
Grases et al., "Effects of phytate and pyrophosphate on brushite and hydroxyapatite crystallization. Comparison with the action of other polyphosphates", Urol Res, Apr. 2000, 28(2), 136-140.
Grases et al., "Phytate (Myo-inositol hexakisphosphate) inhibits cardiovascular calcifications in rats", Front Biosci, Jan. 1, 2006, 11, 136-142.
Grases et al., "A New Procedure to Evaluate the Inhibitory Capacity of Calcium Oxalate Crytallization in Whole Urine," International Urology and Nephrology, May 30, 1995, 27(6), 653-661.
Grases et al., "Artificial Simulation of the Early Stages of renal Stone Formation," British Journal of Urology, Sep. 1994, 74(3), 298-301.
Grases et al., "Study of the Effects of Different Substances on the Early Stages of Papillary Stone Formation," Nephron, Mar. 1996, 73(4), 561-568.
Grases et al., "Anticalculus Effect of a Triclosan Mouthwash Containing Phytate: a Double-Blind, Randomized, Three-Period Crossover Trial", Journal or Periodontal Research, Oct. 2009; Epub: Oct. 22, 2008, 44(5), 616-621.

* cited by examiner

*Primary Examiner* — San-Ming Hui
*Assistant Examiner* — Kathrien Cruz
(74) *Attorney, Agent, or Firm* — Sterne, Kessler, Goldstein & Fox P.L.L.C.

(57) ABSTRACT

The invention relates to a fixed-dose association of 5 phytate and zinc in synergic proportions for use in the treatment of crystallization of hydroxyapatite. Advantageously, said association is in a molar ratio between the phytate and the zinc exceeding 4:1. The invention also relates to the use of said 10 association for manufacturing a drug for the treatment, prophylaxis and/or prevention crystallization of hydroxyapatite in humans.

9 Claims, 3 Drawing Sheets

FIXED-DOSE ASSOCIATION OF PHYTATE AND ZINC

FIELD OF THE INVENTION

The present invention relates to a fixed-dose association of phytate and zinc in synergic proportions for use in the treatment of crystallisation of hydroxyapatite.

The invention also relates to the utilisation of said association for manufacturing a drug for the treatment, prophylaxis and/or prevention of crystallisation of hydroxyapatite in humans.

BACKGROUND OF THE INVENTION

In general, any process of pathological crystallisation is a consequence of an imbalance between three groups of factors: supersaturation, crystallisation promoters (basically heterogeneous nucleants) and repressors of crystallisation (crystallisation inhibitors and cellular defense mechanisms).

A system is supersaturated in relation to a solute when it contains it in amounts exceeding the amount established by its solubility product. It is thus a thermodynamic factor and is only a kinetic question (i.e. of the time elapsed) that the corresponding solid will be finally formed.

The promoters or heterogeneous nucleants are substances that facilitate the formation of the crystal, reducing the induction period by preventing the stage of homogeneous nucleation. These are thus kinetic factors.

The inhibitors of crystallisation are substances that hinder or prevent the development of crystals. They can act at the nucleation level (by adsorbing on the homogeneous or heterogeneous nucleus being formed), of crystalline growth (by adsorbing on the faces of the crystal being formed) or of both processes at once. It therefore also includes kinetic factors.

Myo-inositol hexaphosphate (phytate) is the most powerful inhibitor known of the development of calcium salts, and acts on the heterogeneous nucleation of the calcium oxalate, on the crystalline growth of the calcium oxalate and on homogeneous and heterogeneous nucleation of calcium phosphate. The phytate, together with the pyrophosphate, shows inhibitory effects both on the crystallisation of brushite and crystallisation of hydroxyapatite. Both compounds constitute two of the forms in which the calcium phosphate can crystallise, this last being a majority component of pathological vascular mineralisations.

It has been shown recently that phytate is present in all the organs, tissues and biological fluids of mammals, the human being among them. It has further been shown that most extracellular phytate found in organs, tissues and fluids of mammals has a dietary origin and is not the result of endogenous synthesis, whereas intracellular phytate (found in very much lower concentrations) is probably produced inside the cell. Its levels in the organism are therefore directly related to the exogenous supply thereof, either through dietary ingestion or topical application.

Blood plasma is always supersaturated in relation to calcium phosphate, due to the concentration values of phosphate, calcium and its pH. Indeed, calcifications are frequently found in the cardiovascular system, reducing the flexibility of the blood vessels and promoting thrombosis and arterial rupture. When such calcifications appear in the cardiac valves, they are associated with various disorders which, if not corrected, can lead to heart failure and death.

Various risk factors are now known that are associated with the development of calcifications in the coronary arteries, such as kidney disease, advanced age, high plasma cholesterol levels (a decrease in the cholesterol associated with high-density lipoproteins and increase in the cholesterol associated with low-density lipoproteins), obesity and high triglyceride levels, cytotoxic agents (smoking habit) and bacterial infections.

It must be born in mind that the occurrence of cardiovascular calcifications can start by as early as the second decade of life, and that coronary calcifications affect 50% of people aged between 40 and 49 years, and 80% of people aged between 60 and 69 years.

The precise mechanism of formation of a vascular calcification involves various steps, although in general it requires the prior existence of an injury which acts as an inducer (heterogeneous nucleant) of the calcification (calcium phosphate, generally in the form of hydroxyapatite). Subsequent development of the calcification will depend on the balance of the remaining factors (supersaturation, crystallisation inhibitors, cellular modulators of the calcification).

An important factor in preventing the development of cardiovascular calcifications is therefore the presence of crystallisation inhibitors. A recent document showed the preventive action of phytate on the development of cardiovascular calcifications when the phytate is applied topically (see PCT/IB2004/003588).

In a different field, hydroxyapatite is also accumulated in the buccal cavity through mineralisation of the dental bacterial plaque. Dental bacterial plaque is a deposit on the teeth that cannot be removed with water under pressure or simply by rinsing out the mouth. Brushing does help to prevent a speedy accumulation of such deposits, but even a regular brushing is not enough to remove all the deposits that adhere to the teeth. The plaque that adheres to the surface of the tooth can calcify (calcified dental plaque) to form dental tartar or calculus. The plaque is therefore a precursor of calculus. Unlike the calculus, however, the plaque can be formed on any part of the surface of the tooth, particularly on the gingival margin. Therefore the presence of plaque on the teeth, in addition to being unsightly, can be a precursor to the development of gingivitis and periodontal diseases. There is a direct correlation between the amount of bacterial plaque and the severity of the gingivitis.

The tartar or calculus are calcified deposits on the teeth which are formed due to mineralisation of the plaque, a process that starts within a period of 24-72 hours and takes an average of 12 days to reach maturity. It is made up of organic and inorganic matter with a composition very similar to that of other pathological calcifications observed in the organism (renal lithiasis, calcinosis cutis, etc.):

Organic matter: it mainly comes from microorganisms (bacteria, fungi, etc.) that are connected to one another, forming colonies, although it can also come from food debris remaining in the buccal cavity.

Inorganic matter: it is largely made up of calcium and orthophosphate present in the saliva which are arranged in a crystalline lattice called hydroxyapatite (HAP).

The formation of calculi takes place in two steps. In the first one, the bacterial plaque is deposited on the teeth, being made up of living and dead bacteria surrounded by a gellified matrix derived from bacteria and saliva. In the second step, said plaque undergoes a process of mineralisation until forming the dental calculus. Initially, amorphous calcium phosphate begins to be deposited on and within the extracellular matrix of the dental plaque, which becomes sufficiently packed for the aggregates to be resistant to deformation, in the end turning into the crystalline HAP material. The amorphous calcium phosphate, though related to the HAP, differs from it in its crystalline structure, particle morphology and stoichiometry.

The inhibition of HAP formation has been tested by means of the action of inhibitors, sequestrants, efficient suppressors of calcium and magnesium ions and/or chelating agents. Dehydrated polyphosphates such as water-soluble hexametaphosphates, tripolyphosphates, pyrophosphates and the like have been used for this purpose.

We thus find a list of patents (U.S. Pat. No. 3,488,419; U.S. Pat. No. 4,215,105; U.S. Pat. No. 4,515,772) which utilise or make reference to the use and functions of these polyphosphates proposed to date in oral compositions. However, as disclosed in U.S. Pat. No. 4,627,977, the straight-chain dehydrated polyphosphates are hydrolysed significantly in the oral cavity and/or in the saliva by means of the enzymes in the saliva (phosphatases) into orthophosphates, which do not show any inhibitory action on the formation of HAP; although said hydrolysis is reduced through the combined use of these polyphosphates with fluoride (as disclosed in U.S. Pat. No. 4,808,4109) as well as with the fluoride ion forming part of a polycarboxylate polymer in the document U.S. Pat. No. 4,627,977, an efficient treatment for inhibiting hydroxyapatite has yet to be found.

On the other hand, U.S. Pat. No. 5,300,289 describes antimicrobial oral compositions with phytate for mouth care. The oral compositions described contain phytic acid or pharmaceutically acceptable salt thereof, a cationic antimicrobial compound and compatibilizing agent for the control of the dental calculus, dental plaque, gingivitis, periodontitis and/or bad breath. In particular, it describes a composition comprising: (1) from 0.001 to 10% by weight of one or more compounds having C—O—P bonds, where the compound having the C—O—P bond is myo-inositol hexakis(dihydrogen phosphate), myo-inositol pentakis(dihydrogen phosphate), myo-inositol tetrakis(dihydrogen phosphate) or a physiologically acceptable salt thereof; (2) 0.001 to 10% by weight of one or more cationic antimicrobial compounds; and (3) 0.1 to 20% by weight of one or more compatibilizing agents. As a cationic antimicrobial compound a list of 10 possible compounds or derivatives thereof is disclosed. The compatibilizing agents are chosen from acids and their alkaline metal salts or alkaline earth metal salts, or mixtures thereof. It is also disclosed that the presence of a metallic ion selected from strontium, magnesium, tin, zinc, calcium or mixtures thereof in the aforesaid composition does not lead to precipitation of the phytic acid of the composition in solution and, therefore, the addition thereof to the above composition will help to suppress bad breath. The molar ratio between said metallic ion and the phytic acid can be present in an oral composition from 4:1 to 1:4, preferably from 3:1 to 1:3 and still more preferably, in a 1:1 ratio.

Furthermore, phytate has indeed already been used in oral compositions. Thus, in U.S. Pat. No. 4,259,316 and U.S. Pat. No. 4,335,102 the phytate is used in combination with a compound of tin (II). However, the formation of complexes between phytate and tin are not effective in inhibiting the formation of calculus.

Also, in U.S. Pat. No. 3,934,002, phytate is used in conjunction with a bisbiguanide as an antiplaque and anticaries agent. However, the two compounds react with each other so they cannot be distributed homogeneously throughout the oral composition, to the point that they even form two clearly visible phases.

A large number of compositions have been developed comprising different combinations of antiplaque and antigingivitis agents, together with or optionally together with other compounds such as for example anticalculus agents whose purpose is to eliminate the bacterial etiology and risk factors.

However, there does not yet exist a suitable treatment which permits the inhibition of the crystallisation of hydroxyapatite with good results.

DESCRIPTION OF THE INVENTION

The problem to be solved by the present invention may be posed as an alternative way for inhibiting the crystallisation of hydroxyapatite in human beings, with surprising effects, in particular on the development of dental calculi and on calcification of hydroxyapatite in arteries, veins, heart, brain, lung and skin.

The solution is based on a fixed-dose association of phytate and zinc with synergic effects on the inhibition of hydroxyapatite crystallisation. The combination of phytate and zinc has not been described as a synergic mixture against crystallisation of hydroxyapatite and there is not any explanation of the synergic effect between the phytate and zinc giving rise to an increased inhibiting effect on crystallisation of the phytate against hydroxyapatite.

DEFINITIONS

In the present invention, "phytate" or "myo-inositol hexaphosphate" is taken to mean the molecule corresponding to the formula:

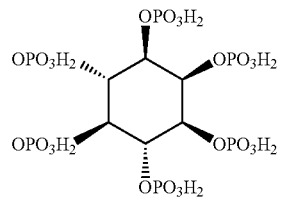

and its corresponding salts, which include but are not limited to sodium, potassium, calcium, magnesium or calcium-magnesium salts.

In the present invention "inhibitor of crystallisation" is taken to mean a substance that is capable of reducing or preventing the formation of mineralisations.

Among the best-known mineralisations are the cardiovascular and buccodental mineralisations or those in other parts of the organism, mainly calcifications, owing to their action of extension of the time of induction of the crystallisation.

In the present invention, "cardiovascular mineralisation" is taken to mean any solid concretion accumulated on the wall of a blood vessel or any part of the heart.

DETAILED DESCRIPTION OF THE INVENTION

The general object of the present invention is to inhibit the formation of hydroxyapatite. Said salt forms mineralisations in the organism which, in general, can be prevented or reduced by the phytate present in the organism. However, where this is not the case there does not yet exist a composition, mixture or treatment that effectively permits the external inhibition of hydroxyapatite crystallisation.

The present invention provides an association of phytate and $Zn^{2+}$ for the treatment, prevention and/or prophylaxis of the formation of hydroxyapatite in the cardiovascular system and buccodental cavity. Likewise, the present invention provides an association of phytate and $Zn^{2+}$ for the treatment, prevention and/or prophylaxis of the formation of hydroxyapatite in the joints, mammary glands, kidney, brain, lung and skin, since the inhibition of crystallisation of a salt in a soft tissue depends on the concentration of inhibitor that can be reached in said tissue. The concentrations of phytate in soft tissues are similar (and in the brain are 10 times higher), so that in these soft tissues the same effect is expected as in cardiovascular tissue.

In particular, the authors of the present invention have found that the presence of zinc in an association of phytate and zinc leads to an increase of the inhibiting effect on the crystallisation of the phytate itself (while the zinc alone has no inhibiting effect on the crystallisation of hydroxyapatite). The zinc is adsorbed on the nucleus being formed or the crystal undergoing growth of hydroxyapatite. As the affinity of the phytate for the zinc exceeds that for calcium, the adsorption of zinc on hydroxyapatite increases the affinity of the phytate for the nucleus being formed or the crystal undergoing growth, enhancing its inhibiting effect on crystallisation.

Surprisingly, it has been found that an association of phytate and zinc at a molar ratio exceeding 4:1 gives rise to an increase in the inhibiting effect of the crystallisation of the phytate of the order of 40%, though always depending on the induction period and the molar ratio of phytate/zinc.

Advantageously, a molar ratio of 5:1, after 10 minutes of crystallisation induction period gives rise to an increased inhibiting effect on crystallisation of phytate of the order of 50% (see FIG. 2).

In the present invention, the synergic effect of an association of phytate and $Zn^{2+}$ on the crystallisation of hydroxyapatite will be shown below. See, in particular, examples 1 and 2 below.

Subsequently, and surprisingly, it will also be proved that an association of phytate and $Zn^{2+}$ inhibits the development of calcifications of hydroxyapatite on fragments of human aortic valve implanted in Wistar rats. The authors of the present invention have found the synergic effect of an association of phytate and $Zn^{2+}$, particularly orally, inhibiting the development of cardiovascular calcifications with excellent results (see Example 3).

The authors of the present invention have also studied the effect of an association of phytate and $Zn^{2+}$ in accordance with the present invention on the formation of hydroxyapatite in the buccodental cavity in an individual submitted to different treatments (see Examples 4 and 5). The objective in this case is to increase the inhibiting capacity of the saliva against the crystallisation of calcium salts and to prevent complications of formation of calcium biomineralisations by using an oral composition comprising an association of phytate and $Zn^{2+}$. The basis for the use of a mouthwash with phytate and $Zn^{2+}$ is the reduction of the risk of formation of hydroxyapatite biomineralisations, and it is grounded on the following facts:

(1) Phytate is a very powerful inhibitor of homogeneous and heterogeneous nucleation and crystalline growth of hydroxyapatite and other calcium phosphates. A consequence of this action is the inhibition of the crystallisation of hydroxyapatite, while the development of microparticles of calcium phosphate adhering to the tooth is prevented.

(2) Phytate is found in human saliva, the concentration thereof varying depending on the diet of the individual.

(3) Certain individuals with salivary deficit of phytate can show sublingual hydroxyapatite calculi.

(4) Phytate has the advantage of being a natural product present in human saliva more resistant to the action of the salivary phosphatases than other linear polyphosphates.

(5) The synergic association of phytate and $Zn^{2+}$ shows more significant in vitro results on inhibition of crystallisation of hydroxyapatite than does the phytate alone.

Therefore, any pharmaceutical form, whether it be a mouthwash, a vitamin supplement or other form of administration comprising a synergic association of phytate and $Zn^{2+}$ in accordance with the present invention is included in the scope thereof.

Figure 1:
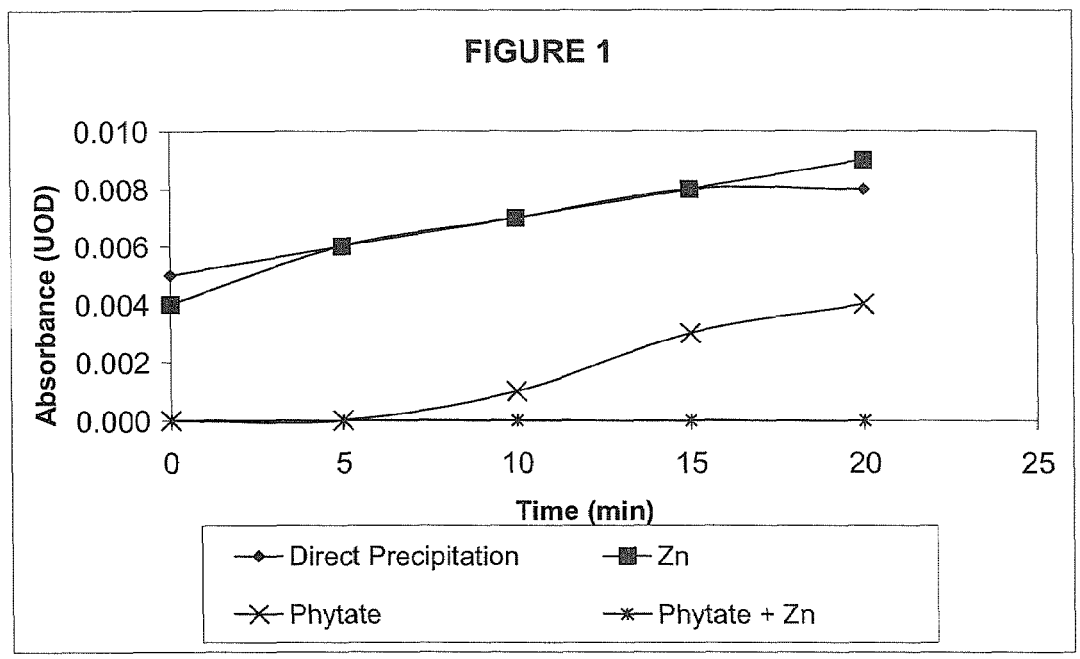
FIG. 1 shows the effect of an association of phytate and $Zn^{2+}$ on hydroxyapatite in vitro.

In said FIG. 1 it is shown that the first curve corresponds to direct precipitation without phytate or $Zn^{2+}$. The second ($Zn^{2+}$) consists of the addition of 0.038 µM of $Zn^{2+}$. As can be observed, no inhibiting effect is shown. The third curve (Phytate) corresponds to the precipitation of hydroxyapatite in the presence of 0.38 µM of phytate. A significant inhibiting effect on crystallisation is shown. Finally, the last graph (Phytate+$Zn^{2+}$) corresponds to the precipitation in the presence of 0.38 µM of phytate and 0.038 µM of $Zn^{2+}$ (phytate-Zn molar ratio 10:1). It can be observed that the precipitation of hydroxyapatite is totally inhibited. Moreover, this is not an additive effect, but a synergic effect, since the Zn alone does not show any inhibiting effect.

Figure 2:
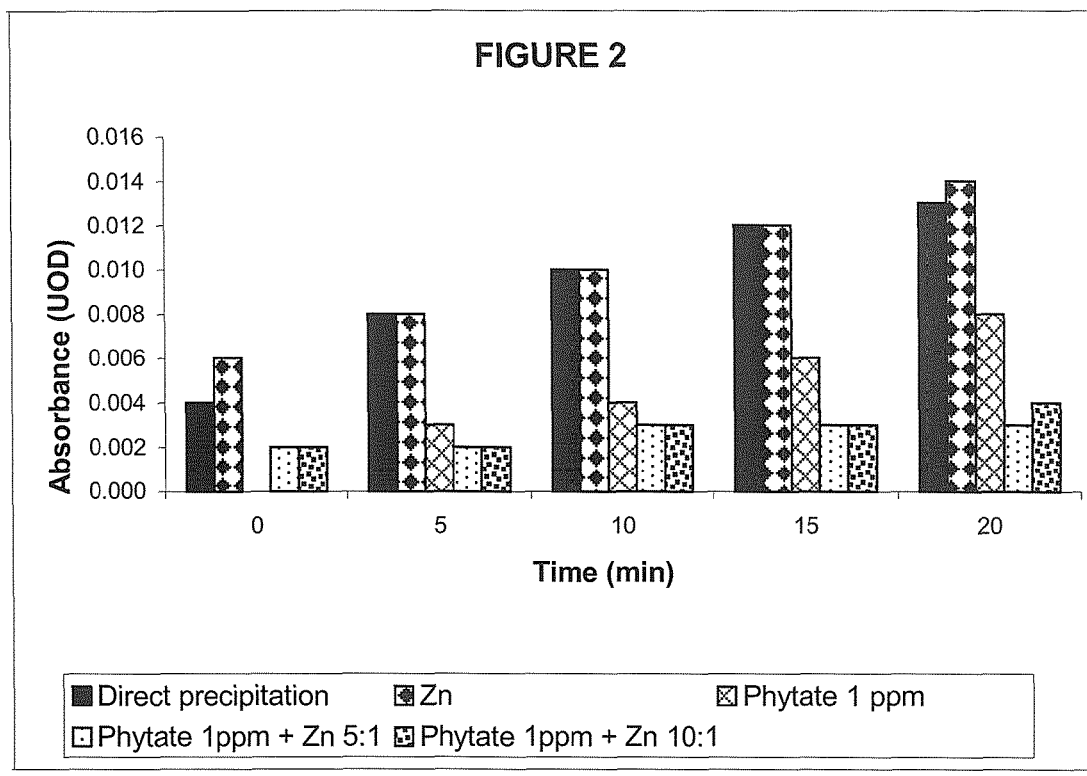

FIG. 2 shows the effect of an association of phytate and $Zn^{2+}$ on hydroxyapatite in vitro.

In said FIG. 2 it is shown that the first series corresponds to the direct precipitation without phytate or $Zn^{2+}$. The second consists of the addition of 0.3 µM of $Zn^{2+}$. As it can be observed, no inhibiting effect is shown. The third series corresponds to the precipitation of hydroxyapatite in the presence of 1.5 µM of phytate. A significant inhibiting effect on crystallisation is shown.

Finally, two series using 1.5 µM phytate and two different concentrations of zinc: $Zn^{2+}$: 0.3 µM (phytate-Zn molar ratio 5:1) and 0.15 µM (phytate-Zn molar ratio 10:1), respectively, are shown. It can be observed that a synergic effect exists between the phytate and the $Zn^{2+}$, since the Zn alone does not show any inhibiting effect.

Figure 3:
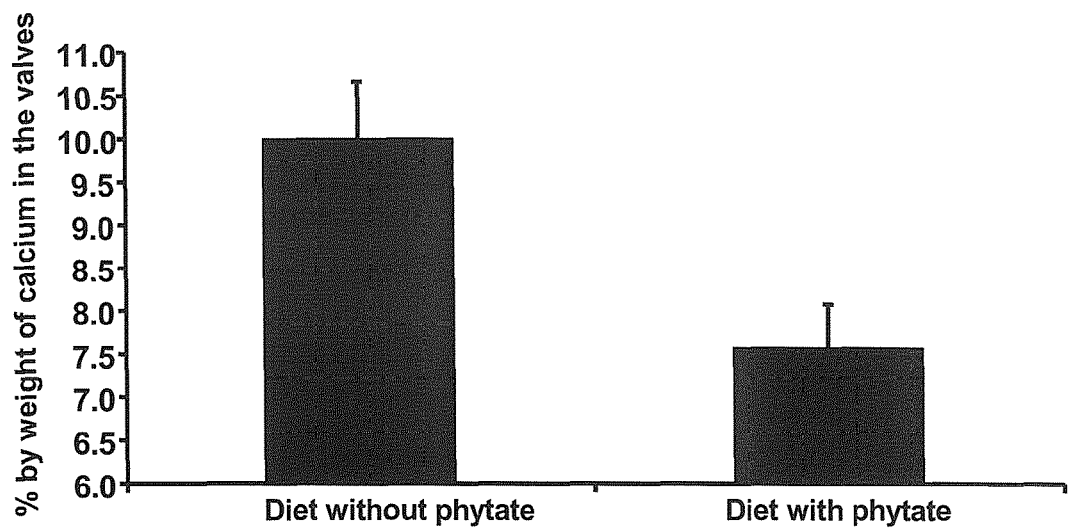

FIG. 3 shows the effect of an association of phytate and $Zn^{2+}$ on the hydroxyapatite formed in human aortic valves implanted in Wistar rats. In said Figure a statistically significant reduction of the degree of calcification in valves can be observed in the group treated with a diet containing phytate+$Zn^{2+}$ in relation to the control group treated with a diet without phytate.

EXAMPLES

The present invention is additionally illustrated by means of the following examples that are non-restrictive of the scope thereof.

Example 1

An in vitro system was designed to study the kinetics of precipitation of hydroxyapatite. A system using the following experimental conditions: [phosphate]=1.5 mM, [$Ca^{2+}$]=60 mg/l, pH=7.5, was used. The kinetics of precipitation of the hydroxyapatite was recorded with a Shimadzu (UV-120-02) spectrophotometer using 3 ml plastic vials and recording the absorbance every 5 minutes at 550 nm. The results are shown in FIG. 1. It can be observed that the precipitation of hydroxyapatite was totally inhibited, with the phytate-Zn synergic mixture, by using the molar ratio of 10:1.

Example 2

With the same system as in example 1, a system using the following experimental conditions: [phosphate]=2.5 mM, [$Ca^{2+}$]=60 mg/l, pH=7.5, was used. The kinetics of precipitation of the hydroxyapatite was recorded with a Shimadzu (UV-120-02) spectrophotometer using 3 ml plastic vials and recording the absorbance every 5 minutes at 550 nm. The results are shown in FIG. 2. It can be observed that a synergic effect exists between the phytate and the $Zn^{2+}$, since the zinc alone does not show any inhibiting effect.

Example 3

Twelve male Wistar rats weighing approximately 250 g (from Harlan Iberica s.l., Barcelona, Spain) were acclimatized for 7 days in our animal facility, whose temperature and humidity conditions were 21±1° C. and 60±5% respectively and with light-darkness cycles of 12:12 hours. The rats were housed in Plexiglas cages, with two rats per cage, and provided with food and drink ad libitum.

Following the acclimatization period, the animals were randomly divided into two groups of 6 rats, a control group, treated only with $Zn^{2+}$, fed with the AIN-76A diet (a purified diet lacking in phytate and with 0.003% of $Zn^{2+}$) and a group treated with the same diet but with a supplement of 1% of phytate in the form of calcium-magnesium salt (phytate-$Zn^{2+}$ molar ratio 30:1). After 16 days each animal was implanted with 2 fragments of uncalcified human aortic valve in the abdominal region. The treatment with the diets was extended for further 30 days after the implantation. After this period, samples of urine were collected at 24-hour intervals to determine the phytate, and subsequently the animals were anaesthetised with pentobarbital (50 mg $kg^{-1}$, i.p.) and the valves were removed and dried.

The surface and the interior of some of the implanted plates were examined by electronic scanning microscopy and compared with fragments of unimplanted valve. The results were as follows: a. Surface of an unimplanted fragment of valve, on which no calcification was shown. b. Surface of a fragment of valve implanted for 30 days in a control group rat, on which a layer of calcium phosphate with aspidinic hydroxyapatite structure was shown. c. Interior of a fragment of valve implanted for 30 days in a control group rat, on which calcium phosphate calcification was shown.

Acid digestion of the plates was then carried out using a $HNO_3$:$HClO_4$ 1:1 mixture, and the total calcium was determined by atomic emission spectroscopy using an inductively coupled plasma (ICP-AES). The results, expressed in percentage by weight of calcium in the fragment, are shown in FIG. 3.

The procedures used in this experiment were carried out in accordance with Directive 86/609/EEC relating to the protection of animals used for experimental and scientific purposes, and an official permission to carry out the experiment was requested by the Ethics Committee of the University of the Balearic Isles.

The urinary levels of phytate at the end of the study were statistically lower in the control group (0.08+/−0.03 mg/l) than in the treated group (1.22+/−0.24 mg/l). The implantation of these valve fragments led to the development of calcifications of calcium phosphate (hydroxyapatite) on the surface of and inside the valve. A statistically significant reduction of the degree of calcification of the aortic valve implanted in the group treated with phytate+$Zn^{2+}$ was shown when compared with the control group (see FIG. 3), thus proving that plasma phytate is capable of inhibiting the development of calcifications of hydroxyapatite formed in human aortic valves implanted in Wistar rats.

Example 4

Firstly, it was decided to evaluate the effect of phytate on the formation of hydroxyapatite in the buccodental cavity. A patient was submitted to two different treatments for one week (Table 1), with two daily administrations of 10 ml of one or the other mouthwashes. A qualitative evaluation was made of the mineralised deposits in the buccodental cavity, and a significant visual reduction of tartar or dental calculus was shown.

TABLE 1

| | Mouthwashes used | |
|---|---|---|
| Compound | Standard mouthwash Concentration (%) | Phytate mouthwash Concentration (%) |
| Water | q.s. | q.s. |
| Ethanol | 10 | 10 |
| Sorbitol | 3 | 3 |
| Potassium phytate | — | 4 |
| Menthol | 0.0425 | 0.0425 |
| Poloxamer 407 | 1 | 1 |
| Trichlosan | 0.012 | 0.012 |
| Dye | 0.015 | 0.015 |

Example 5

Subsequently, a mouthwash with less phytate, combined with $Zn^{2+}$ was used, evaluating after 15 days in a quantitative manner the deposits of hydroxyapatite in buccodental cavity. A patient was submitted to two different treatments for two weeks (Table 2), with twice-daily administrations of 20 ml of one or the other mouthwashes. A quantitative evaluation was made of the mineralised deposits in the buccodental cavity, by collecting mechanically the deposits of plaque and tartar from the patient and sucking them into a filter at a dental clinic, then dissolving the hydroxyapatite present in the deposits with HCl 1M and determining the calcium and the phosphorus by atomic emission spectroscopy using an inductively coupled plasma (Optima 5300DV). A reduction of 95.1% was found in the mineralised deposits of phosphorus and of 88.3% in the calcium.

TABLE 2

| | Mouthwashes used | |
|---|---|---|
| Compound | Standard mouthwash Concentration (%) | Phytate mouthwash Concentration (%) |
| Water | q.s. | q.s. |
| Ethanol | 10 | 10 |
| Sorbitol | 3 | 3 |
| Phytate (potassium) | — | 0.1 |
| Zinc (chloride) | 0.001 | 0.001 (phytate-Zn molar ratio 10:1) |
| Menthol | 0.0425 | 0.0425 |
| Poloxamer 407 | 1 | 1 |
| Trichlosan | 0.012 | 0.012 |
| Dye | 0.015 | 0.015 |

The invention claimed is:

1. A method of treating or inhibiting pathological calcifications of hydroxyapatite in a subject, comprising administering a fixed dose association of phytate and zinc with synergic effect to said subject in need thereof, wherein the zinc is adsorbed on a nucleus being formed or a crystal undergoing growth of hydroxyapatite.

2. The method of claim 1, wherein said association is in a molar ratio between the phytate and the zinc exceeding 4:1.

3. The method of claim 1, wherein said association is in a molar ratio between the phytate and the zinc of 5:1.

4. The method of claim 1, wherein said association is in a molar ratio between the phytate and the zinc exceeding 5:1.

5. The method of claim 1, wherein the calcifications of hydroxyapatite are in the buccodental cavity.

6. The method of claim 5, wherein said association is in the form of a mouthwash.

7. The method of claim 1, wherein said association is in the form of a vitamin supplement.

8. The method of claim 5, wherein the pathological calcifications of hydroxyapatite comprise dental calculi.

9. The method of claim 5, consisting essentially of administering a fixed dose association of phytate and zinc.

* * * * *

UNITED STATES PATENT AND TRADEMARK OFFICE
CERTIFICATE OF CORRECTION

PATENT NO. : 8,377,908 B2  
APPLICATION NO. : 12/279616  
DATED : February 19, 2013  
INVENTOR(S) : Grases Freixedas et al.

Page 1 of 1

It is certified that error appears in the above-identified patent and that said Letters Patent is hereby corrected as shown below:

In The Claims

Column 9, claim 1, line 2, after "hydroxyapatite" insert -- in the buccodental cavity --.

Signed and Sealed this  
Ninth Day of December, 2014

Michelle K. Lee  
*Deputy Director of the United States Patent and Trademark Office*